United States Patent
Martin et al.

(10) Patent No.: US 11,854,780 B2
(45) Date of Patent: Dec. 26, 2023

(54) METHODS, MEDIUMS, AND SYSTEMS FOR IDENTIFYING SAMPLES OF INTEREST BY VECTOR COMPARISON

(71) Applicant: WATERS TECHNOLOGIES IRELAND LIMITED, Dublin (IE)

(72) Inventors: Nathaniel Martin, Stockport (GB); Nicola Lumley, Wilmslow (GB); David S. Douce, Congleton (GB); David Jackson, York (GB)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 0 days.

(21) Appl. No.: 17/500,485

(22) Filed: Oct. 13, 2021

(65) Prior Publication Data

US 2022/0115220 A1    Apr. 14, 2022

Related U.S. Application Data

(60) Provisional application No. 63/091,069, filed on Oct. 13, 2020.

(51) Int. Cl.
*H01J 49/00*    (2006.01)
*G01N 30/72*    (2006.01)
(Continued)

(52) U.S. Cl.
CPC ...... *H01J 49/0036* (2013.01); *G01N 30/7233* (2013.01); *H01J 49/26* (2013.01); *G01N 2030/027* (2013.01)

(58) Field of Classification Search
CPC .. H01J 49/0036; H01J 49/26; G01N 30/7233; G01N 2030/027; G16C 20/20
(Continued)

(56) References Cited

U.S. PATENT DOCUMENTS

2009/0063592 A1*  3/2009  Ivosev ............... H01J 49/0031
2018/0364210 A1* 12/2018  Yao ..................... H01J 49/164

FOREIGN PATENT DOCUMENTS

CN          104572910 A       4/2015
WO    WO-2009029818 A1 *   3/2009   ......... G01N 30/8682

OTHER PUBLICATIONS

International Search Report and Written Opinion for International Patent Application No. PCT/IB2021/059425, dated Jan. 10, 2022.
(Continued)

*Primary Examiner* — Michael Maskell
(74) *Attorney, Agent, or Firm* — Goodwin Procter LLP

(57) ABSTRACT

Exemplary embodiments provide methods, mediums, and systems for comparing a sample of interest to a library of known compounds to quickly determine how similar the sample is to the compounds in the library. Peaks of interest in the sample data are compared to corresponding peaks in the library compound data. These peaks may be represented as vectors, and an angle between the sample vector and the library vector may be used as a similarity metric. In some embodiments, a cosine similarity may be calculated for the vectors. If the similarity score for a given library compound/sample pair exceed a threshold, then the system determines that the library compound and the sample are similar and takes appropriate action. Various parameters associated with the comparison can be adjusted in order to improve the quality of the results and/or the efficiency of the process.

17 Claims, 10 Drawing Sheets

(51) Int. Cl.
*H01J 49/26* (2006.01)
*G01N 30/02* (2006.01)

(58) Field of Classification Search
USPC .............................. 250/281, 282; 702/22–28
See application file for complete search history.

(56) References Cited

OTHER PUBLICATIONS

Lam, H., "Building and Searching Tandem Mass Spectral Libraries for Peptide Identification", Molecular & Cellular Proteomics, 10(12):008565-1 to 008565-10, Dec. 6, 2011.

Stein, S., et al., "Optimization and Testing of Mass Spectral Library Search Algorithms for Compound Identification", Journal of the American Society for Mass Spectrometry, Elsevier Science Inc, US, 5(9):859-866, Sep. 1, 1994.

Samokhin, A., et al., "Evaluation of mass spectral library search algorithms implemented in commercial software", Journal of Mass Spectrometry,50(6):820-825, May 5, 2015.

Cao, L., et al., "Dynamic Multiple Spectral Similarity Measures for Compound Identification", 2013 6th International Congress on Image and Signal Processing (CISP), IEEE, 3:1262-1266, Dec. 16, 2013.

Horlacher, O., et al., "MzJava: An open source library for mass spectrometry data processing", Journal of Proteomics, 129:63-70, Jun. 30, 2015.

International Preliminary Report on Patentability for International Patent Application No. PCT/IB2021/059425, dated Apr. 27, 2023.

\* cited by examiner

Cannabadiol

THC

METHODS, MEDIUMS, AND SYSTEMS FOR IDENTIFYING SAMPLES OF INTEREST BY VECTOR COMPARISON

CROSS-REFERENCE TO RELATED APPLICATIONS

This application claims the benefit of U.S. Provisional Patent Application No. 63/091,069, filed Oct. 13, 2020. The entire disclosure of which is hereby incorporated by reference.

BACKGROUND

Mass spectrometry (MS) and liquid chromatography-mass spectrometry (LCMS) apparatuses are used to analyze a chemical sample to study the identity, mass, or structure of the sample. Other types of devices also exist for sample analysis, including infrared spectrometers and gas spectrometers. Although IS and GS devices may be able to provide more detailed information that MS devices, they also tend to be more complex, expensive, and difficult to operate. Because of this, they may require significantly more time to precisely analyze a sample.

BRIEF SUMMARY

Exemplary embodiments provide methods, mediums, and systems for comparing a sample of interest to a library of known compounds to quickly determine how similar the sample is to the compounds in the library.

According to a first embodiment, a system may receive a sample of interest at a mass spectrometry (MS) device for analysis. The sample of interest may be analyzed with the MS device, where the analyzing involves generating a plurality of spectrums for the sample of interest. The plurality of spectrums may be broken into bins (e.g., based on spectrum intensity values).

The system may access a sample library that includes ionization information for known compounds. For each known compound in the sample library, a plurality of key peaks for the compound may be retrieved. The key peaks for the respective compound may be compared to a set of spectrum bins from the sample of interest. This may involve representing the key peaks for the respective compound and the set of spectrum bins as vectors, computing a similarity value corresponding to a difference in angle between the vectors, and comparing the similarity value to a similarity threshold.

In some embodiments, the spectrum bins may be the most prominent spectrum bins from the sample of interest. In others, the system may refrain from performing binning on the spectrum as a whole—instead, it may identify any peak in the spectrum and then select an area around the peak within a predefined or dynamically-selected margin of the peak. This selected area may serve as a bin for comparison purposes.

After comparing the similarity value to the similarity threshold, the system may identify that the sample of interest is similar to the respective compound (if the similarity value exceeds the similarity threshold). The system may then output an indication that the sample of interest is similar to the respective compound in response to the identifying.

The similarity is determined simply by comparing a relatively small number of key peaks from the sample of interest to corresponding peaks from the compounds in the library. Accordingly, the system can determine the similarity much more quickly and efficiently than if the system tried to make a positive identification of the sample.

One difference between identifying a similarity and positively identifying the sample is that identifying the similarity is not probabilistic. In other words, the system is able to discern that the sample is similar to a compound from the library, but does not necessarily determine how likely it was that the two compounds would be similar (although this feature could be added with an additional cost in computation and time). For example, the system may identify a similarity between the sample and a cannabinoid, but it may still be possible that many non-cannabinoid compounds are similar to cannabinoids. Thus, the system does not give a probability that the sample is a cannabinoid; it only states that the compound shares similarities with cannabinoids. Nonetheless, a similarity is often enough to make an initial determination for further follow-up, or to make decisions in situations where speed is essential.

Furthermore, because the similarity is computed as a difference in angle between two vectors, the similarity can be determined based on simple equations with a relatively small number of inputs, further improving the efficiency and speed of the process. Because n mass/intensity values can be represented in an n-dimensional vector space quite readily, relying on the angle between the sample and library vectors is an effective way to quickly determine the similarity.

According to a second embodiment,

According to a third embodiment, the plurality of spectrums may consist of four spectrums. Although embodiments could be implemented with more or fewer spectrums, four spectrums yields a good balance of processing efficiency and specificity. Therefore, the similarity can be determined quickly, but with good accuracy.

According to a fourth embodiment, the system may receive, as an input from a user, a user-defined number of most-prominent bins for comparison to the key peaks. This adjustability allows a user to select more peaks (for increased accuracy) or fewer peaks (for increased processing efficiency) for comparison.

According to a fifth embodiment, the system may receive, as an input, a user-defined value for the similarity threshold. Depending on the user's tolerance for false positives or negatives, the user is thus empowered to adjust the required level of similarity for a library compound to be considered a "hit" or "miss" against the sample.

According to a sixth embodiment, the difference in angle between the vectors may be represented as a cosine similarity value. This provides a particularly fast and simple way to measure the similarity between the two samples in the context described above.

According to a seventh embodiment, the bins may be weighted based on the spectrum intensity value and/or mass associated with each bin.

By weighting higher masses greater than lower masses, it makes higher mass fragments count more towards the end result. Because MS precursors and larger fragments tend to be more reliable and useful measurements (more diagnostic), and because it may be helpful to emphasize the precursor especially, it is helpful to provide greater significance to higher masses. This can be achieved by applying an augmenting weight directly to the higher-massed bins (and/or a reducing weight to lower-massed bins), by multiplying the intensity of each bin by its mass, and/or raising a bin intensity to a higher power, such as $mass^2$.

By weighting lower intensity readings so that they count for more than they otherwise would, one can avoid the situation where a few large peaks dominate the result. Often, there may be a significant drop-off in intensity after a few large peaks, with the risk being that these few large peaks "set the result." Other smaller peaks might not be considered, even though they might include useful information. One possibility is to raise the intensity numbers to a power less than one (e.g., taking their square root), which compresses the differences between high and low intensities.

According to an eighth embodiment, the system may receive, as input, a user-defined bin weighting. By making the bin weightings tunable, the user can customize the process to their particular data set (e.g., emphasizing mass weightings if the peaks in the sample and/or library tend to be more concentrated among low-mass fragments, or emphasizing lower intensity readings if there is a significant drop-off in intensities in the sample and/or library data).

According to a ninth embodiment, a bin from one of the plurality of spectrums may be weighted over bins from others of the plurality of spectrums. For example, certain voltages might be more informative than others when making comparisons. The system might therefore weight a low-voltage mass spectrum over higher voltage mass spectrums. In some embodiments, the weighting might be performed by first comparing the sample and library mass spectrums for a first voltage, and determining if the similarity is sufficient to justify processing the remaining spectrums. This conserves processing resources by only performing a full analysis on compounds that are most likely to be similar to the sample.

According to a tenth embodiment, for each of the bins, a ratio between an intensity of the bin and an intensity of a bin having the highest intensity value may be computed. Any bins that have a ratio lower than an intensity ratio threshold may be filtered out. If a library match is performed on data that has not been filtered for intensity, it may be possible to generate a vector for any mass value. This increases the chance of getting false positives when similarity is determined based on an angle between these vectors. Removing any vectors below a certain threshold (e.g., 5% of the peak intensity of the largest peak) thus reduces the false positivity rate.

According to a eleventh embodiment, the intensity ratio threshold referenced above may be user-defined and may be received as an input. By enabling a user to set the threshold, the user can accept more or less risk of false positives, as the application requires.

Any of the above embodiments may be implemented as instructions stored on a non-transitory computer-readable storage medium and/or embodied as an apparatus with a memory and a processor configured to perform the actions described above.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
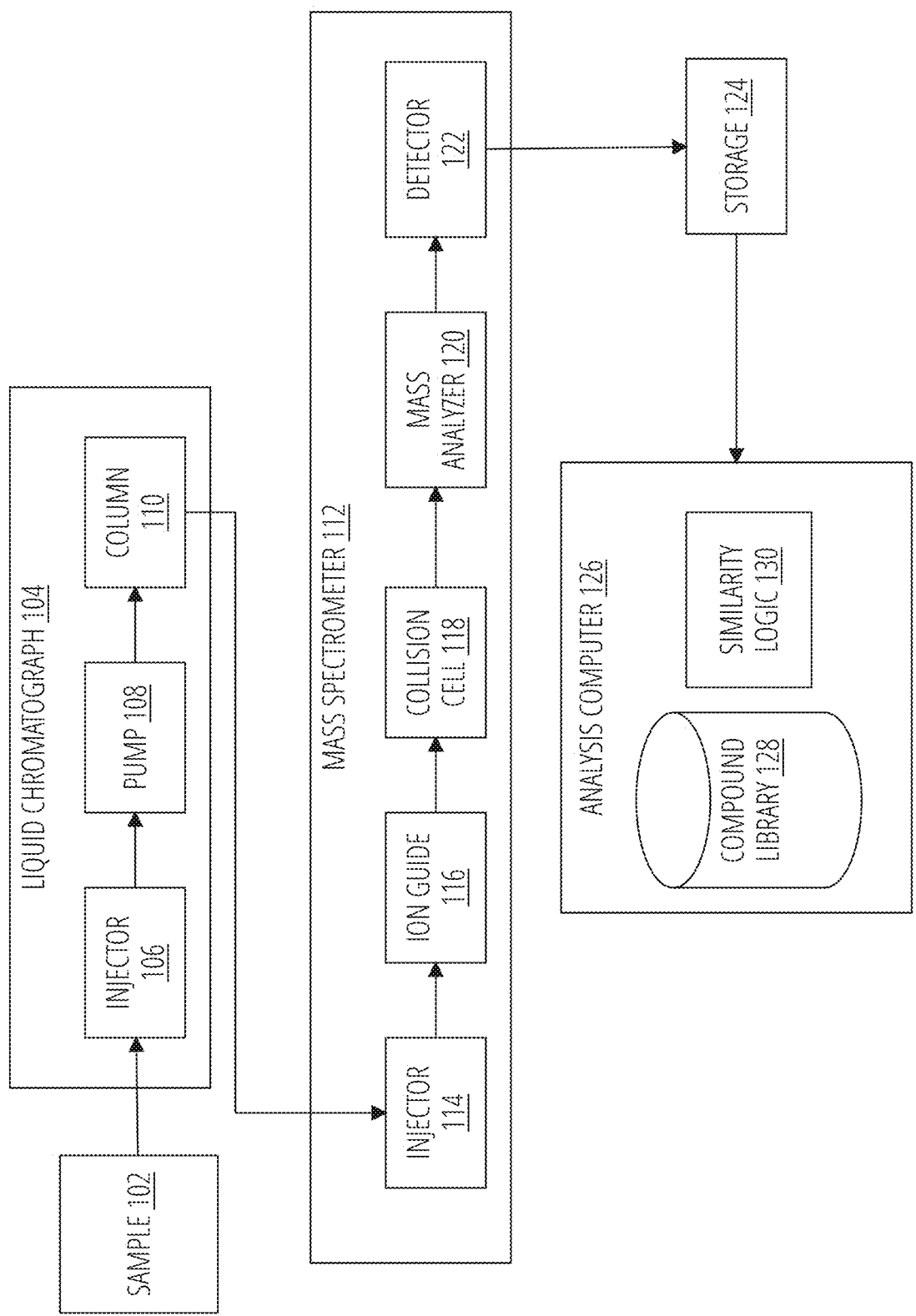
FIG. 1 illustrates an example of a mass spectrometry system according to an exemplary embodiment.

In some cases, it may not be necessary to precisely identify a sample, which might take a great deal of time. Instead, it may be useful to quickly determine whether the analyzed sample is within a category of substances.

For instance, consider a situation where a bag of white powder is found and there is a question as to whether the bag contains an illicit substance. An MS device may be capable of accepting a sample of the powder, analyzing the sample to determine its chemical makeup, and then determining the precise elements making up the powder. However, this process might take 25-30 minutes, which might be prohibitive in certain situations. Moreover, at the end of the process, the result might be that the sample is merely sugar or flour, meaning that the time used to analyze the sample might have been better spent doing other tasks or analyzing other samples. It may be more useful to receive a faster but less specific response (e.g., whether the powder is an opioid or not), rather than trying to more specifically classify the substance.

Such a capability would be useful in a variety of applications. For example, when a surgeon is removing a tumor, it would be helpful to know whether the surgeon is cutting into healthy or cancerous tissue. Taking 25-30 minutes to identify the specific makeup of the tissue means that the surgeon would not be able to use the results during the surgery. On the other hand, a simple "yes" or "no," obtained relatively quickly, could be used to guide the surgery and ensure that only unhealthy tissue is removed. Other situations in which this capability might be helpful include screening urine or blood for toxicology, food authenticity, speciation, characterization of plant phenotyping, and other applications where answers are desired in real- or near-real-time. Another application could include screening blood from a newborn against a library of known newborn diseases and conditions.

Exemplary embodiments accept a sample of interest and analyze it with a mass spectrometry (MS) apparatus. The results of the analysis are compared to a library of similar results from known samples, allowing a binary decision to be made (e.g., "matches library" or "does not match library") very quickly.

More specifically, the sample may be analyzed by subjecting it to a variety of voltages in the MS apparatus to break the sample into constituent components. Each voltage may yield a different mass spectrum for the sample. The sample's mass spectrums may then be simplified or digitized by chopping the spectrums up into "bins" of different intensities. This may allow the most prominent peaks in the samples to be identified.

The binned peaks from the sample may be compared to a library of known compounds. In the library, each known compound may be associated with data representing prominent peaks in one or more mass spectrums. The system may perform various data processing (normalization, weighting, etc., as described in more detail below) to prepare the sample data and/or the library data for comparison. The system may then compute a similarity value indicating how similar the sample is to one or more of the compounds in the library. For example, the system may represent the data from the sample and the data from the library as different vectors, and may then compute a cosine similarity value that compares the sample vector to the library vector(s). The similarity value may be compared to a threshold to determine whether the sample is sufficiently similar to the compound(s) in the library. If so, the system outputs an identification of the similarity.

Because of the simplicity of this approach, results can be received very quickly—even on a computing device having fewer hardware resources.

Moreover, various parameters that control the above-described process can be customized to yield better results. For example, parameters that can be tuned include the maximum number of peaks to be compared between the library compound and the sample, the weighting for each peak based on its intensity and/or mass, filtering thresholds based on intensity or some other value, the similarity threshold, and which voltage spectrums to emphasize, among other possibilities. Because the system is so highly tunable, it can be configured to run more or less efficiently (e.g., by considering fewer or more peaks, respectively), and to filter out more or fewer results (depending on the user's tolerance for false positives).

Note that, although techniques are described below with respect to MS devices, the principles described may also be applied to other types of devices, including IS and GS devices.

Exemplary embodiments described herein provide techniques for identifying samples of interest by comparing ionization data from the samples with a library of known compounds. In real time or near-real time, the system matches the compounds of the library file against each sample, and reports a score indicating the strength of the match against each compound. Rather than breaking down the sample into elements or molecules and then For purposes of illustration, FIG. 1 is a schematic diagram of a system that may be used in connection with techniques herein. Although FIG. 1 depicts particular types of devices in a specific LCMS configuration, one of ordinary skill in the art will understand that different types of devices (e.g., MS, tandem MS, etc.) may also be used in connection with the present disclosure. It is also noted that, when the present disclosure refers to tuning an "MS apparatus," any part of the system used in conjunction with the mass spectrometer 112 (such as the liquid chromatograph 104) may be encompassed by this term.

A sample 102 is injected into a liquid chromatograph 104 through an injector 106. A pump 108 pumps the sample through a column 110 to separate the mixture into component parts according to retention time through the column.

The output from the column is input to a mass spectrometer 112 for analysis. Initially, the sample is desolved and ionized by a desolvation/ionization device 114. Desolvation can be any technique for desolvation, including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization technique. Ions resulting from the ionization are fed to a collision cell 118 by a voltage gradient being applied to an ion guide 116. Collision cell 118 can be used to pass the ions (low-energy) or to fragment the ions (high-energy).

Different techniques (including one described in U.S. Pat. No. 6,717,130, to Bateman et al., which is incorporated by reference herein) may be used in which an alternating voltage can be applied across the collision cell 118 to cause fragmentation. Spectra are collected for the precursors at low-energy (no collisions) and fragments at high-energy (results of collisions).

The output of collision cell 118 is input to a mass analyzer 120. Mass analyzer 120 can be any mass analyzer, including quadrupole, time-of-flight (TOF), ion trap, magnetic sector mass analyzers as well as combinations thereof. A detector 122 detects ions emanating from mass analyzer 122. Detector 122 can be integral with mass analyzer 120. For example, in the case of a TOF mass analyzer, detector 122 can be a microchannel plate detector that counts intensity of ions, i.e., counts numbers of ions impinging it.

A storage 124 may provide permanent storage for storing the ion counts for analysis. For example, storage 124 can be an internal or external computer data storage device such as a disk, flash-based storage, and the like. An analysis computer 126 analyzes the stored data. Data can also be analyzed in real time without requiring storage in a storage medium 124. In real time analysis, detector 122 passes data to be analyzed directly to computer 126 without first storing it to permanent storage.

Collision cell 118 performs fragmentation of the precursor ions. Fragmentation can be used to determine the primary sequence of a peptide and subsequently lead to the identity of the originating protein. Collision cell 118 includes a gas such as helium, argon, nitrogen, air, or methane. When a charged precursor interacts with gas atoms, the resulting collisions can fragment the precursor by breaking it up into resulting fragment ions. Such fragmentation can be accomplished as using techniques described in Bateman by switching the voltage in a collision cell between a low voltage state (e.g., low energy, <5 V) which obtains MS spectra of the peptide precursor, with a high voltage state (e.g., high or elevated energy, >15V) which obtains MS spectra of the collisionally induced fragments of the precursors. High and low voltage may be referred to as high and low energy, since a high or low voltage respectively is used to impart kinetic energy to an ion.

Various protocols can be used to determine when and how to switch the voltage for such an MS/MS acquisition. For example, conventional methods trigger the voltage in either a targeted or data dependent mode (data-dependent analysis, DDA). These methods also include a coupled, gas-phase isolation (or pre-selection) of the targeted precursor. The low-energy spectra are obtained and examined by the software in real-time. When a desired mass reaches a specified intensity value in the low-energy spectrum, the voltage in the collision cell is switched to the high-energy state. The high-energy spectra are then obtained for the pre-selected precursor ion. These spectra contain fragments of the precursor peptide seen at low energy. After sufficient high-energy spectra are collected, the data acquisition reverts to low-energy in a continued search for precursor masses of suitable intensities for high-energy collisional analysis.

Different suitable methods may be used with a system as described herein to obtain ion information such as for precursor and product ions in connection with mass spectrometry for an analyzed sample. Although conventional switching techniques can be employed, embodiments may also use techniques described in Bateman which may be characterized as a fragmentation protocol in which the voltage is switched in a simple alternating cycle. This switching is done at a high enough frequency so that multiple high- and multiple low-energy spectra are contained within a single chromatographic peak. Unlike conventional switching protocols, the cycle is independent of the content of the data. Such switching techniques described in Bateman, provide for effectively simultaneous mass analysis of both precursor and product ions. In Bateman, using a high- and low-energy switching protocol may be applied as part of an LC/MS analysis of a single injection of a peptide mixture. In data acquired from the single injection or experimental run, the low-energy spectra contains ions primarily from unfragmented precursors, while the high-energy spectra contain ions primarily from fragmented precursors. For example, a portion of a precursor ion may be fragmented to form product ions, and the precursor and product ions are substantially simultaneously analyzed, either at the same time or, for example, in rapid succession through application of rapidly switching or alternating voltage to a collision cell of an MS module between a low voltage (e.g., generate primarily precursors) and a high or elevated voltage (e.g. generate primarily fragments) to regulate fragmentation. Operation of the MS in accordance with the foregoing techniques of Bateman by rapid succession of alternating between high (or elevated) and low energy may also be referred to herein as the Bateman technique and the high-low protocol.

In summary, such as when operating the system using the Bateman technique, a sample 102 is injected into the LC/MS system. The LC/MS system produces two sets of spectra, a set of low-energy spectra and a set of high-energy spectra. The set of low-energy spectra contain primarily ions associated with precursors. The set of high-energy spectra contain primarily ions associated with fragments. These spectra are stored in a storage medium 124. After data acquisition, these spectra can be extracted from the storage medium and displayed and processed by post-acquisition algorithms in the analysis computer 126

The data acquired by the high-low protocol allows for the accurate determination of the retention times, mass-to-charge ratios, and intensities of all ions collected in both low- and high-energy modes. In general, different ions are seen in the two different modes, and the spectra acquired in each mode may then be further analyzed separately or in combination.

The ions from a common precursor as seen in one or both modes will share the same retention times (and thus have substantially the same scan times) and peak shapes. The high-low protocol allows the meaningful comparison of different characteristics of the ions within a single mode and between modes. This comparison can then be used to group ions seen in both low-energy and high-energy spectra.

Note that, in exemplary embodiments described herein, this technique may be expanded to provide any desired number of spectra. For example, instead of high and low spectra, the MS apparatus may be configured to provide four spectra arising from applying four different voltages. The voltages may be selected on a compound-by-compound basis. Generally, the lowest voltage may represent the smallest amount of voltage that will cause an analyzed compound to fragment consistently; more rigid structures may require more voltage to break. The highest voltage may represent the largest amount of voltage that yields results consistently exhibiting noise below a predetermined noise limit. The two intermediate voltages may be spaced evenly apart from the low and high voltage, or may be selected to yield data that is considered particularly interesting.

The captured data from a sample of interest that is stored in the storage 124 may be compared to a compound library 128. The compound library 128 may include, for a number of known compounds, various data about the compounds. In addition to other data, the compound library 128 may specify, for each data entry pertaining to a compound, a voltage at which the data was acquired, and any intensity peaks that were noted in the data. The intensity peaks may be specified as a tuple combining the mass at which the value was acquired, and the intensity value for the given mass. The entry may also identify the number of such peaks. The identification of peaks in MS data is a procedure that will be known to one of ordinary skill in the art, and is not described here for the sake of brevity. If more than one spectrum was acquired for a given compound, the library may include multiple entries for the compound, one for each spectrum. An example of a portion of a library as it might be stored in a data structure is reproduced below:

Name: Benzocaine
Formula: C9H11NO2
MW: 165
ExactMass: 165.078979
DB#: 2
Comments:
<conditions><polarity>pos</polarity><cv>30</cv><rt>0.000</rt></conditions>
Num Peaks: 8
77 86; 92 71; 94 623; 120 831; 121 67;
138 999; 139 74; 166 376;
Name: Benzocaine
Formula: C9H11NO2
MW: 165
ExactMass: 165.078979
DB#: 3
Comments:
<conditions><polarity>pos</polarity><cv>50</cv><rt>0.000</rt></conditions>
Num Peaks: 7
65 447; 77 999; 92 548; 93 212; 94 635;
120 991; 138 141;
Name: Benzocaine
Formula: C9H11NO2
MW: 165
ExactMass: 165.078979
DB#: 4
Comments:
<conditions><polarity>pos</polarity><cv>70</cv><rt>0.000</rt></conditions>
Num Peaks: 7
65 999; 66 168; 77 740; 92 360; 93 172;
94 74; 120 94;

The entries in the compound library 128 may be compared to the mass spectrum generated by the MS apparatus using similarity logic 130. Examples of similarity logic 130 are described in more detail below in connection with FIG. 3A, FIG. 3B, and FIG. 9.

Figure 2:
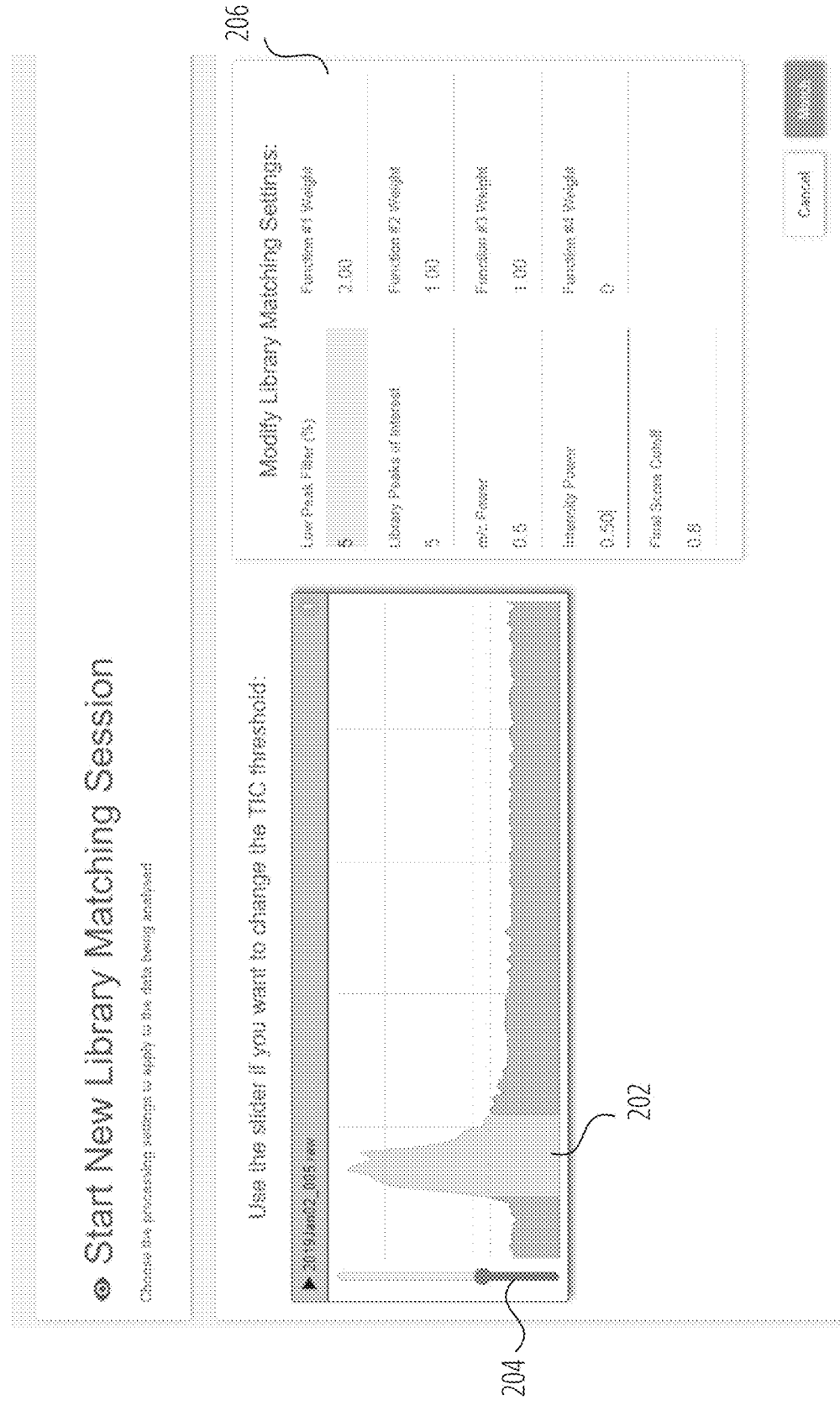
FIG. 2 illustrates a user interface for configuring comparison parameters in accordance with one embodiment.

In order to generate comparison results, a user may adjust one or more comparison parameters. FIG. 2 depicts an exemplary interface suitable for adjusting the parameters.

One portion of the interface depicts the spectral data for the sample of interest, including a highlighted region of interest 202. Because the spectral data may include noise and other non-relevant data (for purposes of the comparison), the system automatically selects a region of interest 202 (typically including the bulk of the intensity peaks in the data) and highlights it for user review. The user can adjust the size of the region of interest 202 by moving a slider 204.

Furthermore, the system provides a parameter settings interface 206 allowing the user to adjust various settings used for the comparison. For ease of reading, an example of settings that can be adjusted are depicted in Table 1 below:

TABLE 1

| Setting | Value |
| --- | --- |
| Low Peak Filter (%) | 5 |
| Library Peaks of Interest | 5 |
| Intensity Power | 0.5 |
| m/z Power | 0.5 |
| Final Score Cutoff | 0.8 |
| Function #1 Weight | 2 |
| Function #2 Weight | 1 |
| Function #3 Weight | 1 |
| Function #4 Weight | 0 |

Any of these settings may be input by a user. If the user does not specify a setting, it may default to a default value.

As shown above, the settings include a low peak filter, which specifies a minimum ratio or percentage that a peak in the spectrum must reach (as compared to the maximum peak size) in order to be considered in the comparison analysis. In this example, the low peak filter is set to remove peaks that are less than 5% of the intensity of the highest peak in the data.

The settings further include a number of library peaks of interest. This parameter sets a ceiling on the number of peaks in each spectrum for a compound in the library that will be compared to the sample of interest. In this example, at most five peaks will be included in the analysis. If a library compound does not include five peaks (e.g., if the compound includes only four peaks), then the total number of peaks in the library's data entry for the compound may be used. If the library compound includes exactly five peaks, then those five peaks may be used. If the library compound includes more than five peaks, then the five most-prominent peaks (e.g., those with the highest intensity values) may be selected.

The intensity power represents a scaling exponent to be applied to the intensity of the peaks. As noted above, this has the effect of compressing the differences between different intensities, which increases the effect of lower intensities and reduces the chance that large peaks will dominate the result.

The mass/charge (m/z) power represents the exponent to which the m/z value is raised. This has the effect of making higher masses count for more in the result, which gives emphasis to precursor and larger fragments.

The final score cutoff may indicate the minimum similarity value required for the sample of interest to be considered similar to a library compound. If the similarity value is below the final cutoff score, the system may consider the sample and library compound to be non-similar. If the similarity value is above the threshold, the library compound may be included in a list of compounds considered to be similar to the sample of interest. The list may be ranked by similarity value, stored in a computer-readable medium, and/or displayed on an interface.

The weights for Function #1-4 may represent the weighting assigned to each different spectra resulting from applying different voltages to the sample of interest and/or library compounds. In one embodiment, Function #1 may represent the lowest voltage, Function #2 the second-lowest, etc. As noted above, it may be desirable to give Function #1 the highest weight, since this data tends to screen out more library compounds from the comparison.

Figure 3A:
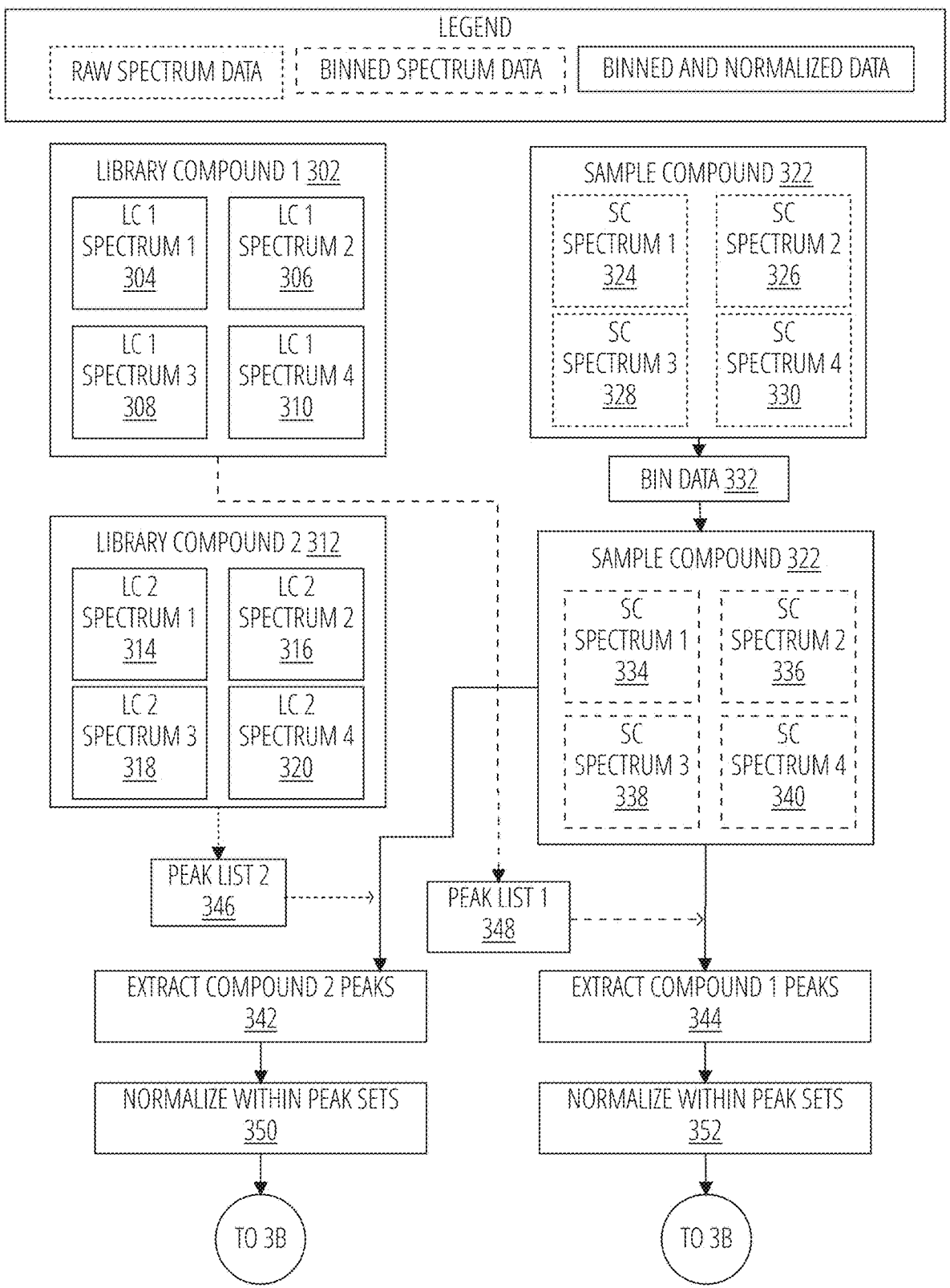
FIG. 3A and FIG. 3B are data flow diagrams depicting how library and sample data are processed in accordance with one embodiment.
Figure 3B:
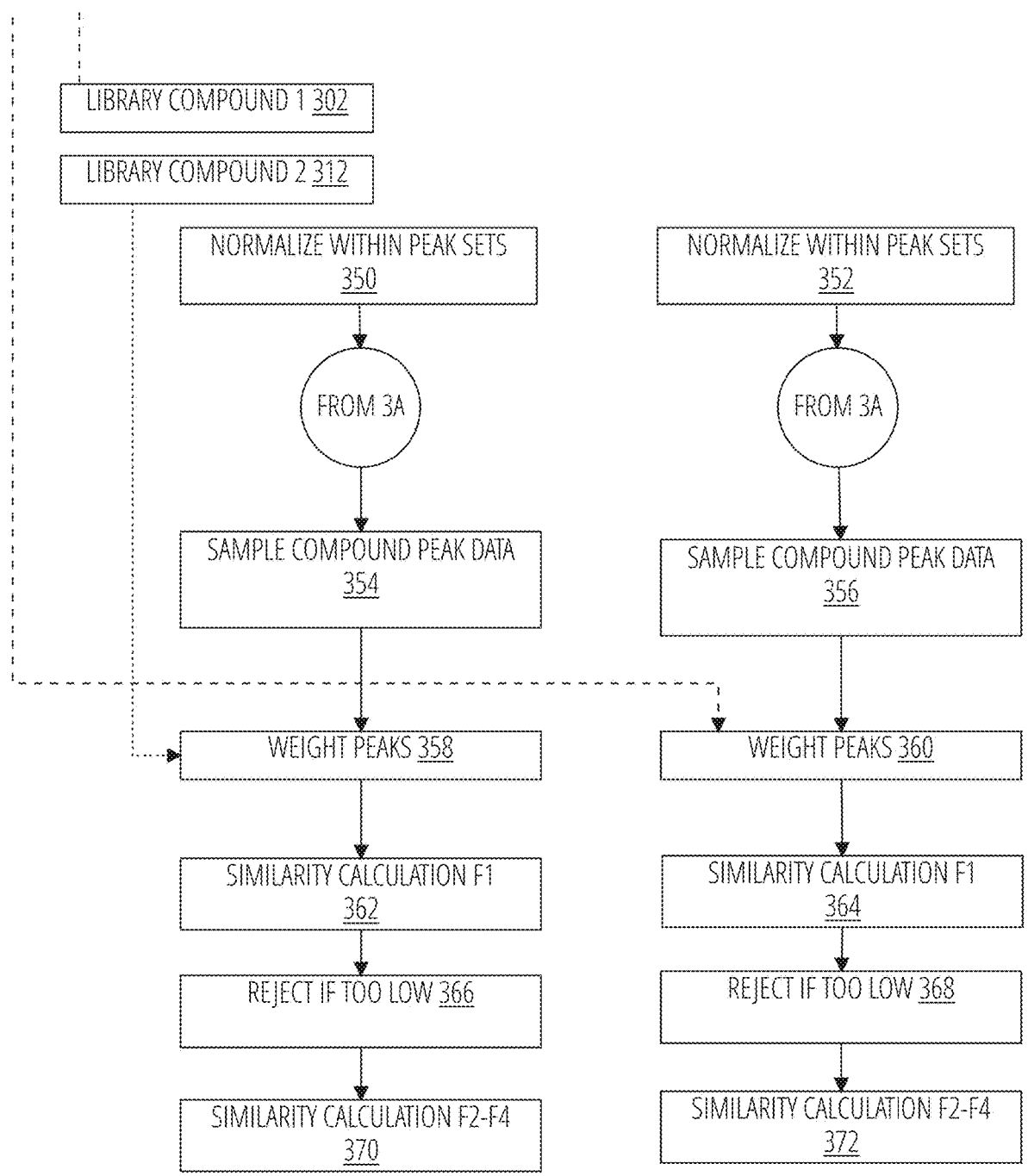

FIGS. 3A and 3B are data flow diagrams showing information exchange according to an exemplary embodiment. Although this flow diagram depicts a particular example for purposes of illustration, it is contemplated that different configurations (involving different numbers of peaks, different numbers of compounds in the library, different numbers of voltages, and variations in processing steps) may also be applied. Although the depicted example shows the same number of peaks in each compound and the sample of interest, this is not required; if there is a mismatch between the number of peaks, a predetermined or user-specified number of most prominent peaks may be selected for comparison, subject to the explanation provided in connection with FIG. 4.

The library may store spectral data for a number of compounds, such as library compound 1 302 and library compound 2 312. Each library compound is associated with peak data, such as the depicted values for LC 1 Spectrum 1 304, LC 1 Spectrum 2 306, LC 1 Spectrum 3 308, LC 1 Spectrum 4 310, LC 2 Spectrum 1 314, LC 2 Spectrum 2 316, LC 2 Spectrum 3 318, LC 2 Spectrum 4 320. The peak data for the compounds stored in the library may, at this stage of processing, already be normalized and binned.

"Normalization" refers to a process of putting selected peaks on the same scale. In mass spectrometry, normalization may be done to correct for a shift in signal that is not due to a real change in a peak of interest. For example, if two different spectra are compared, but one spectrum's signals are twice as high due to technical instrument factors, then one might correct for this to determine if a peak of interest changes in levels after correcting for global distortions in signal.

As noted above, some of the spectra corresponding to different voltages may be weighted more than others. This can shift the weighted vector's value on one axis, but not necessarily on another, which changes the angle between the vectors. Thus, it may be important to normalize the data onto the same scale so that the different functions can be compared fairly. Furthermore, as shown in FIG. 3A and FIG. 3B, the data in the library may already be normalized whereas the sample data is not; in this case, normalization allows for an apples-to-apples comparison.

Importantly, scaling a vector by multiplying its values linearly does not change the underlying angle between the scaled vector and another vector. Thus, normalization will not affect the similarity metric described herein, which relies on the angles between the vectors.

"Binning" refers to simplifying the data by digitizing it (chopping it into a set number of "bins"). For example, the data may be binned at a 1 m/z resolution with the center of the bins being whole-number values. For example, a binned signal at m/z 200 may include the integrated signal from m/z 199.5 to m/z 200.5. Binning the data in this way is far simpler than performing peak detection, and hence can be done quickly and efficiently. The exact height of a specific peak is not taken into account, so much as the integrated value within the bin. If a signal exists for a library compound in bin 200, then that value is compared to the sample of interest's value in bin 200. Therefore, alignment and peak matching do not need to occur.

In an alternative embodiment, the system may perform peak detection to a limited degree. For example, a peak may be detected in the data and then a margin around the peak may be defined. The margin may be a predetermined margin, or may be dynamically determined (e.g., based on the shape of the detected peak). The peak and surrounding margin may serve as a bin for the purposes described below. This process may be performed for a single peak or a predetermined number of peaks.

As noted above, the data for the compounds in the library may already be normalized and binned. However, the data for the sample compound 322 may or may not be. In the example depicted in FIG. 3A, the data for the sample of interest is neither normalized nor binned.

At block 332, the sample data may be binned as described above. This allows the format of the sample data to match the format of the library data. In one embodiment, the data values may be binned at a 1 m/z resolution with the center of the bins being whole number values. The value assigned to each bin may represent the integrated signal from the previous bin to the next bin.

The sample data is not yet normalized, because it will be normalized later after peaks of interest are selected for comparison. Because different peaks may be selected for comparison to different library compounds (see FIG. 4), normalization occurs after these peaks have been selected.

To that end, peaks are next selected for comparison. For each library compound, a list of peaks (e.g., peak list 1 348 and peak list 2 346) may be retrieved from the library. The number of peaks selected may be determined by a predetermined default value or by the user-selected values described above in connection with FIG. 2. For each of the library compounds, the system may extract (at block 342 and block 344, respectively) the binned values from the sample compound in the m/z bins corresponding to the peaks from the peak lists.

The system may then (at block 350 and block 352) normalize within the peak sets. In order to normalize the data at this stage, the system may divide the intensity of each peak in the sample compound set that is relevant to the match (as determined in block 342 and block 344) by the intensity of the highest peak in the sample compound data set; this gives a scaling factor of 1 (in the case of the highest peak) or less (in the case of the other peaks in the sample compound data). This value for each peak is multiplied by 999, which results in the highest peak taking a value of 999 and each other peak gaining a scaled value. The results may be rounded to the nearest whole value so that the data accuracy for the sample and the library match.

In some cases, the highest peak in the library data will be the same peak as the highest peak in the sample data, as in the example from Table 2 below (where the highest peak is indicated in bold).

TABLE 2

| m/z | Intensity of Library Peak | Intensity of Sample Peak | Normalized Intensity of Sample Peak |
| --- | --- | --- | --- |
| 115 | 215 | 191 | 223 |
| 443 | 999 | 855 | 999 |
| 449 | 292 | 398 | 465 |
| 775 | 550 | 546 | 638 |
| 965 | 436 | 423 | 494 |

In other cases, the highest peak may differ between the library data and the sample data, as in the example in Table 3. In this situation, the highest peak in the sample data should be selected and the other sample data should be normalized to this peak.

TABLE 3

| m/z | Intensity of Library Peak | Intensity of Sample Peak | Normalized Intensity of Sample Peak |
| --- | --- | --- | --- |
| 115 | 215 | 34 | 56 |
| 443 | 999 | 407 | 674 |
| 449 | 292 | 363 | 601 |
| 775 | 550 | 603 | 999 |
| 965 | 436 | 520 | 861 |

Turning to FIG. 3B, after the data is normalized within the peak sets, the result may be normalized sample compound peak data 354 for the peaks within the sample compound spectrum that are relevant to library compound 2 312 and normalized sample compound peak data 356 for the peaks within the sample compound spectrum that are relevant to library compound 1 302. Of course, where the library includes more compounds, the above-described and below-described procedures may be repeated for each library compound.

Figure 5:
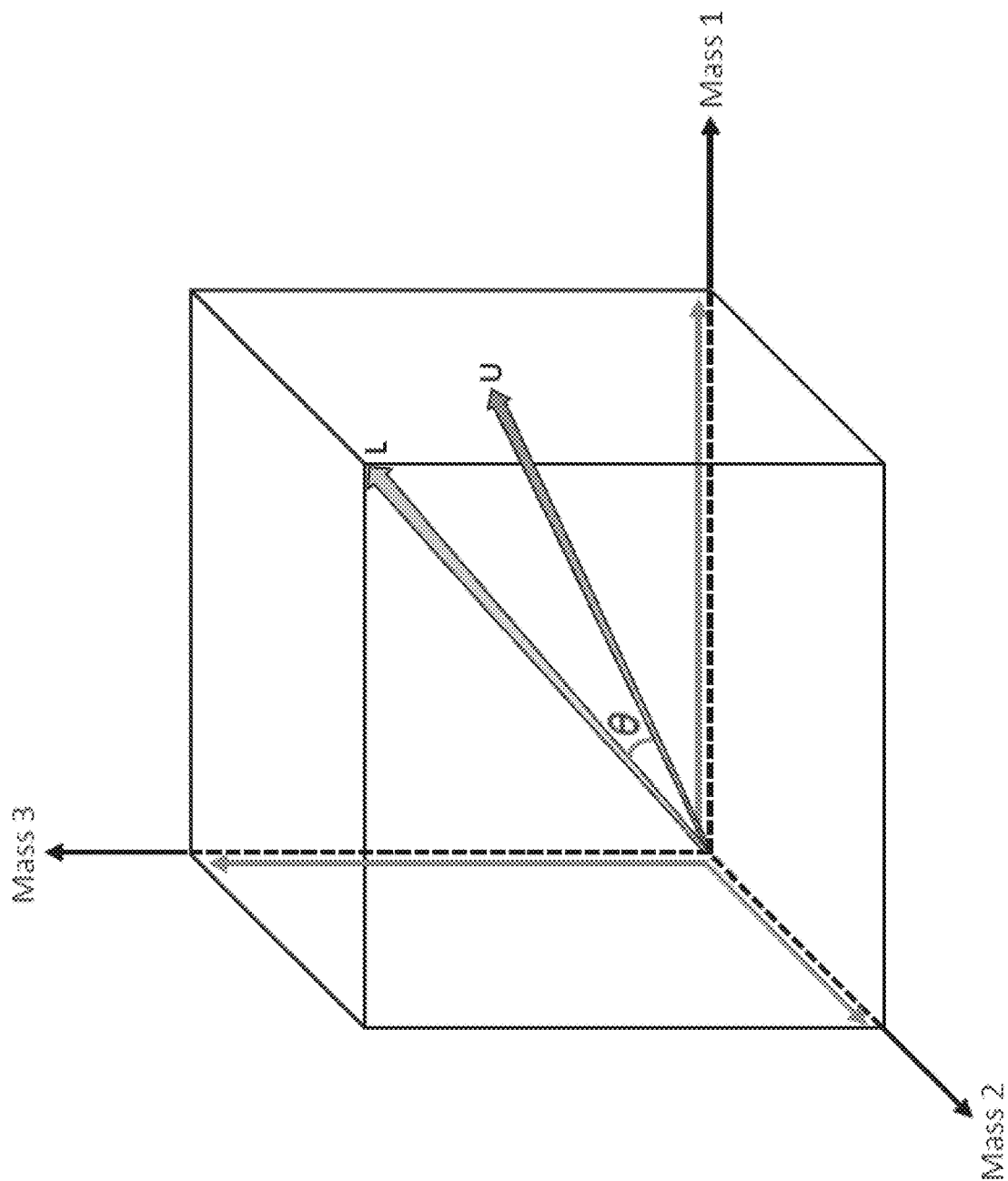
FIG. 5 illustrates an example of a similarity metric in accordance with one embodiment.

The system may then, at block 358 and block 360, weight the peaks based on mass and intensity by applying predetermined or user-defined weighting factors, as described above. In one embodiment, the weighting may apply Equation 1 below:

$$W = \left(\frac{m}{z}\right)^a (I)^b (F) \quad \text{Equation 1}$$

where:
W=the weighted peak intensity value
m/z=the mass/charge value for the bin in question
I=the normalized intensity value for the peak of the bin in question
a=the m/z power, specified by the user or a predefined value (2 is a reasonable default value)
b=the intensity power, specified by the user or a predefined value (0.5 is a reasonable default value)
F=the weighting applied to the function (voltage) that gave rise to the spectrum being weighted The system may then perform similarity calculation F1 364 and similarity calculation F1 364 by comparing the sample compound to the first and second library compounds. This may be achieved (in this example using two library compounds) by creating four vectors: a first vector representing the sample compound peak data 356 that were selected for comparison to library compound 1 302; a second vector representing the peaks selected for comparison from library compound 1 302; a third vector representing the sample compound peak data 354 that were selected for comparison to library compound 2 312; and a fourth vector representing the peaks selected for comparison from library compound 2 312. The system may then compute the angle between the first vector and the second vector, and similarly for the angle between the third vector and the fourth vector. Similar compounds will have relatively small angles between their respective vectors, while dissimilar compounds will have relatively large angles. Thus, a similarity value may be calculated based on the angle between the vectors. One conceptual technique for understanding the above-described vectors is depicted in FIG. 5.

One example of a technique for calculating the difference in the angles between the vectors is a cosine similarity calculation. Cosine similarity may be calculated according to Equation 2, below:

$$\text{Cosine Similarity} = \frac{\sum_{i=1}^{n} x_i y_i}{\sqrt{\sum_{i=1}^{n} x_i^2} \sqrt{\sum_{i=1}^{n} y_i^2}} \quad \text{Equation 2}$$

where $x_i$ and $y_i$ are each set of the corresponding values from the sets of data being compared (in this example, the readings in each data set for the same m/z bin). More generally, Equation 2 multiplies the intensity for a mass in sample x by the intensity of the same mass in sample y, and then sums these values across the various available masses/bins. This value is then divided by the Pythagorean length of the x-vector (computed by summing all the x-values after squaring them, and square rooting the sum, then multiplying this value by the equivalent value for the y-vector).

In some embodiments, each of the functions F1-F4 corresponding to the different voltages/spectra may be combined into a single vector, and an angle between the vector for the sample and the vector for the library compound may be computed. However, a slightly different approach is taken in FIG. 3B. In this example, the intensity values for the first spectrum only (corresponding to Function F1 having the lowest voltage) are converted to vectors at block 362 and block 364. The similarity between the vectors for the F1 function only are computed and compared to a threshold value. At block 366 and block 368, it is determined if the similarities are below the threshold. If so, the library compound is rejected as being dissimilar and processing does not need to proceed to consider Functions F2-F4. Otherwise, at block 370 and block 372, similarity calculations are made for Functions F2-F4; if the result of any of these calculations is a similarity score that exceeds the similarity threshold, then the library compound in question is flagged as being similar to the sample compound. Any library compounds that were found to be similar may be listed and ranked by their similarity scores, and the most similar compound may be displayed and highlighted on an interface (see, e.g., FIG. 6). The results of the comparisons may be store in a non-transitory computer readable medium.

Figure 4:
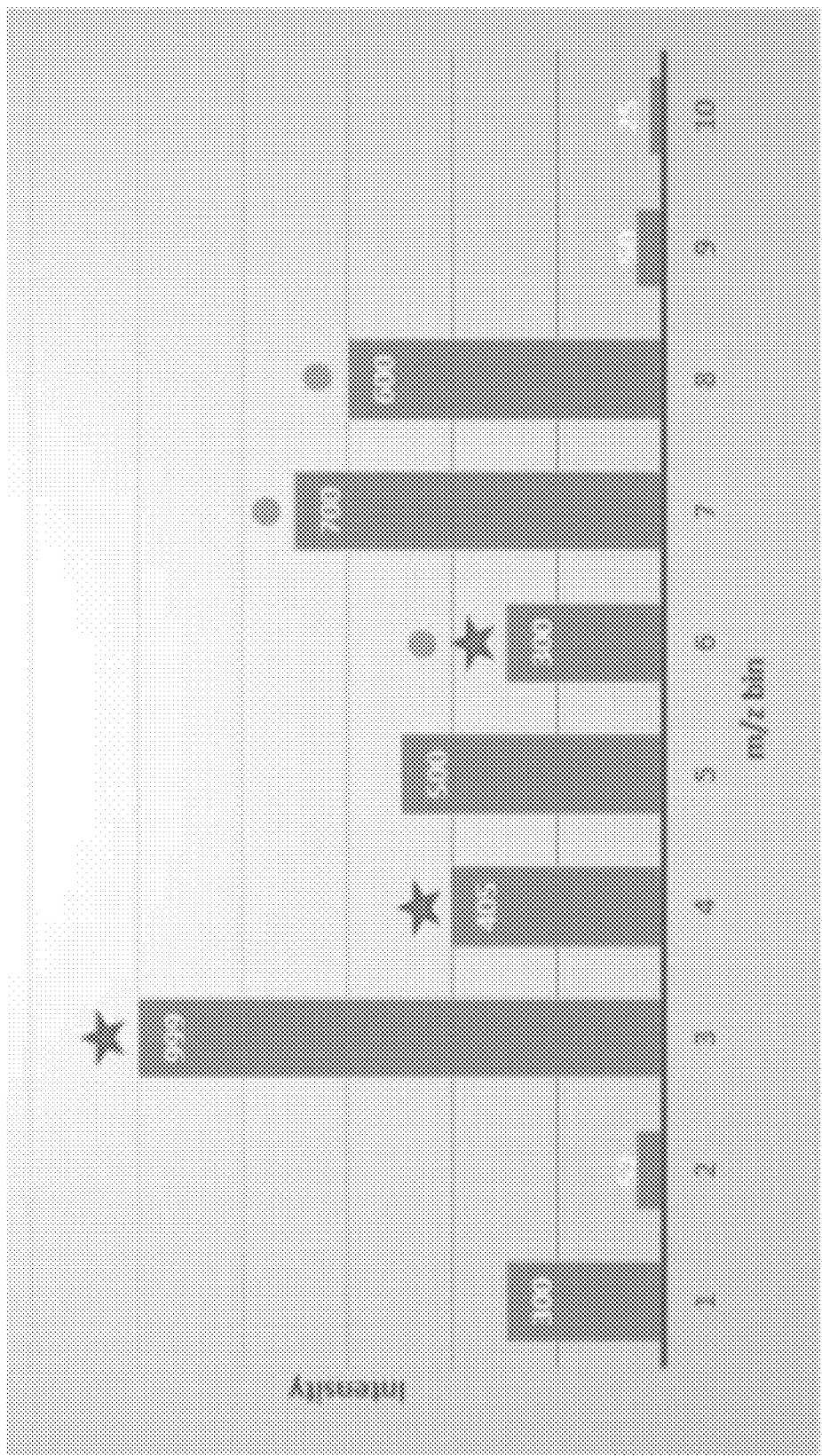
FIG. 4 illustrates an example of comparing sample peaks to two different library compounds in accordance with one embodiment.

FIG. 4 depicts an exemplary spectrogram showing intensities for each of 10 binned mass/charge values. The intensity value for each bin is illustrated on the respective bars. As shown in this example, the most prominent peak falls in m/z bin 3, and has an intensity value of 999.

In FIG. 4, peaks 3, 7, and 8 are associated with the highest intensity values. However, the system may be configured to match only those peaks in the sample that are also relevant to the library compounds; only the relevant bins are extracted for comparison to each library compound. For example, the first library compound may have peaks at bins 3, 4, and 6 (indicated by stars in FIG. 4). Thus, when comparing the sample of interest to the first library compound, only peaks 3, 4 and 6 may be considered. On the other hand, a second library compound may have peaks at m/z bins 6, 7, and 8. When comparing the sample of interest to the second library compound, only peaks 6, 7, and 8 may be considered.

As noted above, the intensity values may be normalized so that the highest peak is set to a value of 999 and other peaks are scaled to corresponding values. Note that, when the sample data is normalized in FIG. 3A, the data is normalized with respect to the library compound that is under consideration. Thus, when normalizing for the first library compound as noted above, with peaks at 3, 4, and 6, the data is normalized to the highest value of these selected peaks (peak 3). In this case, peak 3 already has an intensity value of 999, so nothing further needs to be done to scale the data. On the other hand, when normalizing for the second library compound, bins 6, 7, and 8 are selected. The highest value among these peaks is in bin 7, and so bin 7's intensity value of 700 is scaled up to 999 and the remaining peaks are adjusted proportionally.

The above-described vectors may be conceptualized according to the example depicted in FIG. 5.

The vectors may be calculated by defining an n-dimensional space, where n corresponds to the number of peaks in the data under consideration. Each axis in the n-dimensional space may correspond to one m/z bin. The values for each bin may then be plotted on its respective axis, and a vector pointing towards the value on the axis may be computed. These results may be combined by summing the vectors to define a combined vector whose length and direction depend on the lengths and directions of the individual bin vectors. FIG. 5 depicts an example where two vectors, U and L, have been defined in a three-dimensional space.

It will be clear from that description that if the sample has peaks of the exact same values as the peaks of a library compound, then the resulting vectors will be identical and the angle θ between them will be 0. If the peaks are different, then the angle θ between the vectors will be greater the more the underlying values diverge.

Figure 6:
FIG. 6 illustrates an example of a user interface showing comparison results in accordance with one embodiment.
Figure 7A:
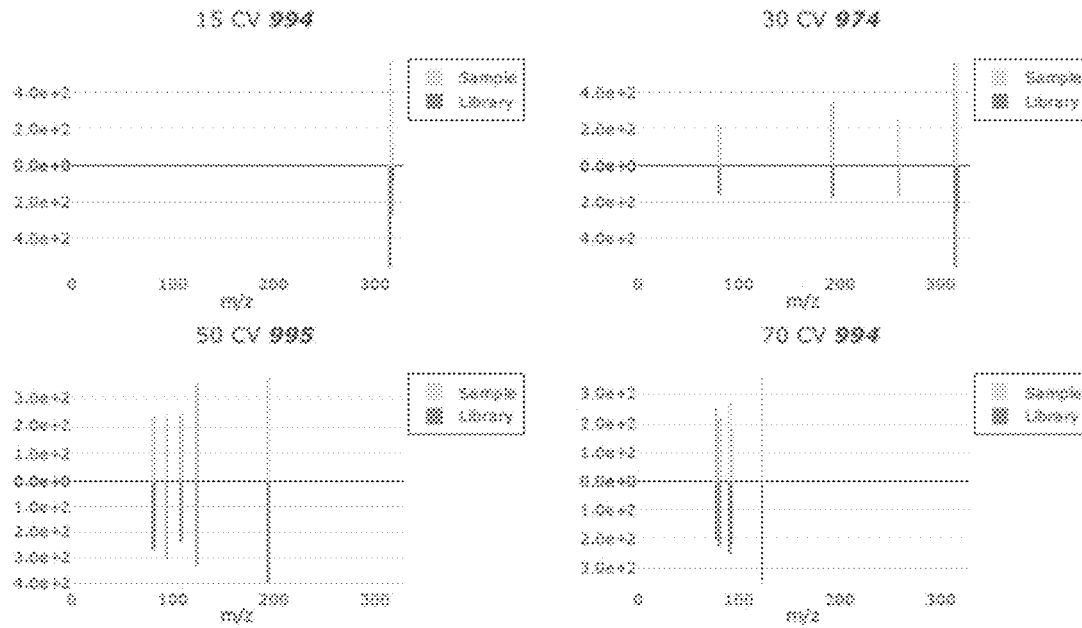
FIG. 7A and FIG. 7B depict user interfaces showing comparisons of a sample to first and second compounds from a library, respectively.
Figure 7B:
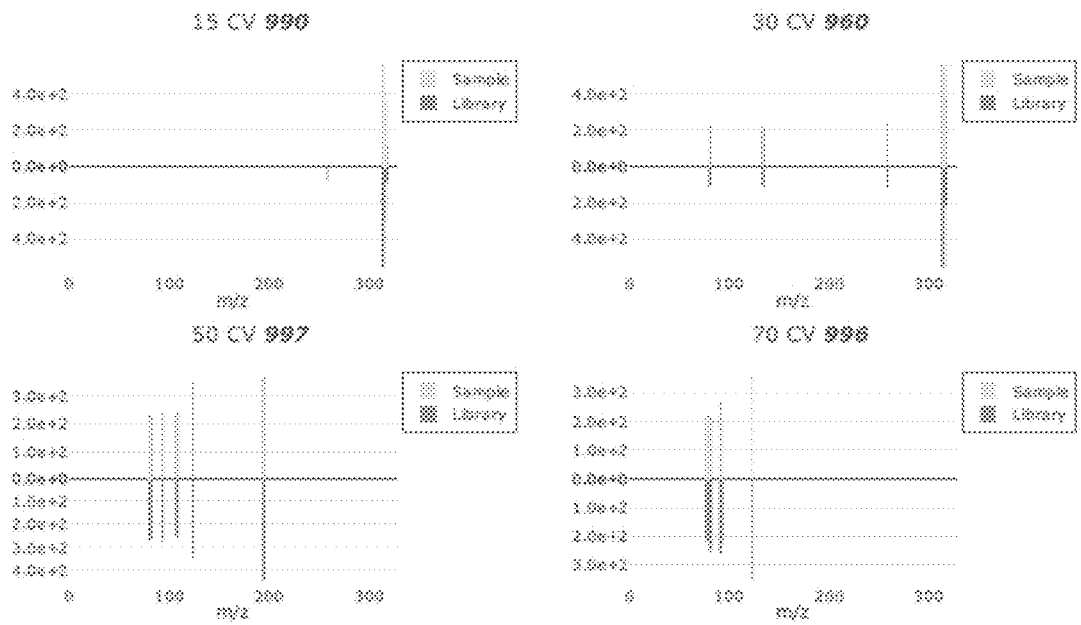

FIG. 6 depicts an exemplary interface for displaying the results of the comparison between the sample of interest and the library. In this example, each of the compounds from the library to which the sample was compared are depicted in a panel on the right side of the screen, along with their similarity scores. In some embodiments, only those compounds whose similarity scores exceeded the similarity threshold are displayed, with the most-similar compound being displayed at the top of the list, highlighted, or otherwise visually distinguished. In other embodiments, all the compounds in the library that were tested may be displayed and ranked, and those whose similarity scores exceeded the similarity metric may be highlighted. If desired, a user can select one of the compounds in the display to view a comparison between the selected peaks from the library compound as compared to the sample of interest, as shown in FIG. 7A (for the cannabidiol library compound) and FIG. 7B (for the THC library compound).

Figure 8:
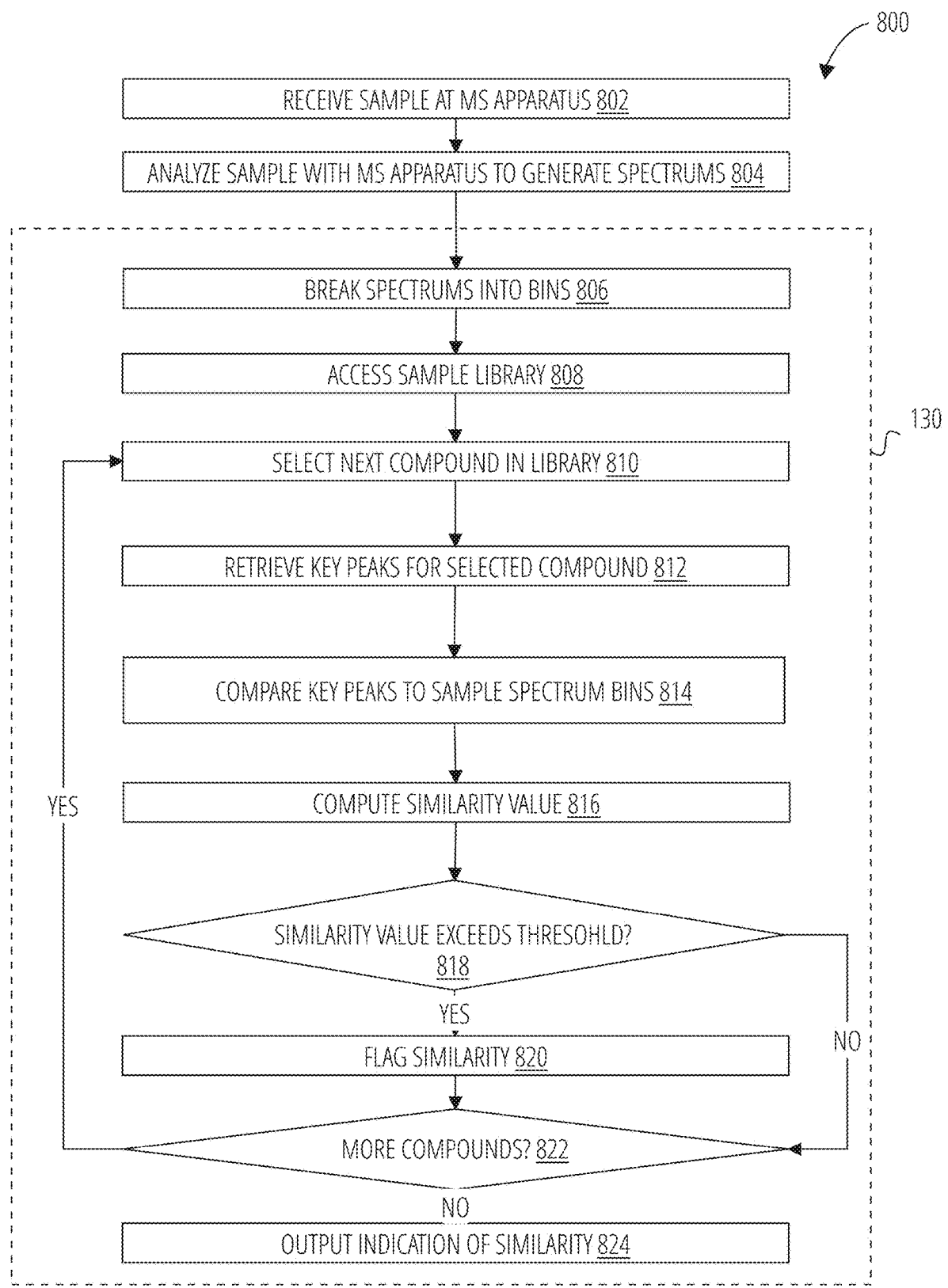
FIG. 8 illustrates a comparison process 800 in accordance with one embodiment.

FIG. 8 depicts an exemplary comparison process 800 in accordance with an exemplary embodiment. Although FIG. 8 depicts logical blocks in a certain arrangement, one of ordinary skill in the art will understand that exemplary embodiments may be implemented with more, fewer, or different logical blocks than those depicted. The comparison process 800 may be embodied as instructions stored on a non-transitory computer-readable medium, where the instructions are configured to cause a processor to perform the actions described in connection with each logical block.

At block 802, a sample of interest may be received at an MS apparatus. At block 804, the sample of interest may be analyzed by the MS apparatus to generate one or more spectra. In one embodiment, the MS apparatus operates to generate four spectra.

At block 806, the system may break the spectra from block 804 into bins. This may be performed in the manner described above in connection with block 332 from FIG. 3A; for the sake of conciseness, this description is not repeated here.

At block 808, the system may access a sample library. For example, the system may download the sample library (or entries from the sample library) remotely, or may access a local copy of the sample library stored on the system. The sample library may include binned and normalized data for various spectra for different compounds of interest.

At block 810, the system may select the next compound in the library for analysis. If the user specifies particular compounds to be analyzed, the system may select the next compound for analysis from the user's list.

At block 812, the system may retrieve the key peaks for the selected compound. This may be performed in the manner described above in connection with peak list 1 348 and peak list 2 346 from FIG. 3A; for the sake of conciseness, this description is not repeated here.

At block 814, the system may compare key peaks from the library compound to corresponding peaks from the sample compound. This may be performed in the manner described above in connection with block 342 through block 360 from FIG. 3A and FIG. 3B; for the sake of conciseness, this description is not repeated here.

At block 816, the system may calculate a similarity value for the comparison performed in block 814. This may be performed in the manner described above in connection with block 362 through block 372 from FIG. 3B; for the sake of conciseness, this description is not repeated here.

At decision block 818, the system may determine if the similarity value exceeds a threshold, which may be predetermined or user-specified. If not, processing proceeds to decision block 822, and the system determines if more library compounds remain for analysis.

If the determination at decision block 818 is "YES," then processing may proceed to block 820 and the library compound may be flagged as similar to the sample compound. Processing may then proceed to decision block 822.

At decision block 822, the system determines if all available library compounds (or all library compounds selected by the user) have been analyzed. If not, processing reverts to block 810 and the next library compound is analyzed. If so, processing proceeds to block 824 and the system outputs an indication of the similarity. This may involve storing the similarity scores in a non-transitory computer-readable medium, transmitting the similarity scores over a network, displaying a results interface such as the ones depicted in FIG. 6, FIG. 7A, and FIG. 7B, etc. Processing may then terminate.

Figure 9:
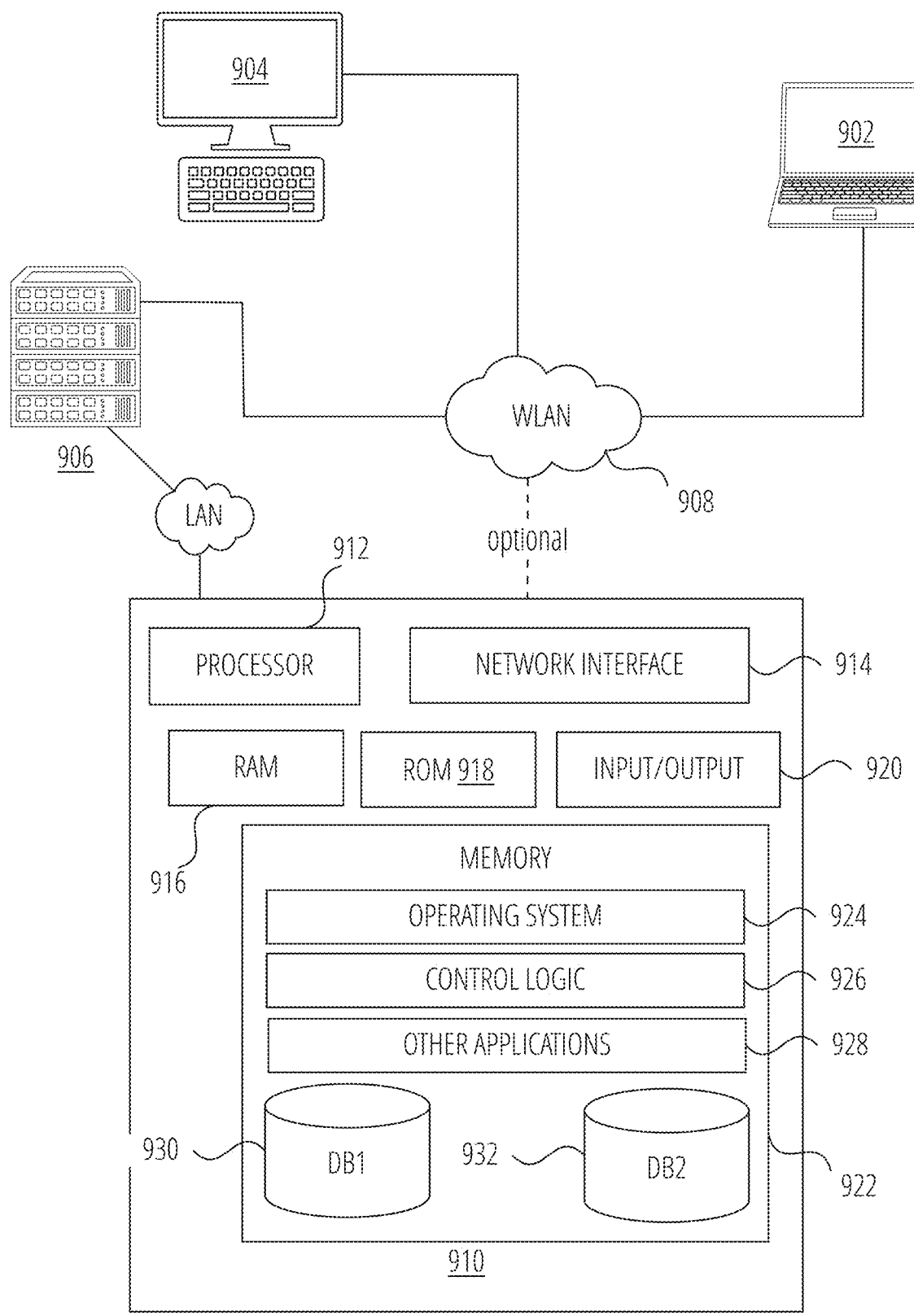
FIG. 9 depicts an illustrative computer system architecture that may be used to practice exemplary embodiments described herein.

FIG. 9 illustrates one example of a system architecture and data processing device that may be used to implement one or more illustrative aspects described herein in a standalone and/or networked environment. Various network nodes, such as the data server 910, web server 906, computer 904, and laptop 902 may be interconnected via a wide area network 908 (WAN), such as the internet. Other networks may also or alternatively be used, including private intranets, corporate networks, LANs, metropolitan area networks (MANs) wireless networks, personal networks (PANs), and the like. Network 908 is for illustration purposes and may be replaced with fewer or additional computer networks. A local area network (LAN) may have one or more of any known LAN topology and may use one or more of a variety of different protocols, such as ethernet. Devices data server 910, web server 906, computer 904, laptop 902 and other devices (not shown) may be connected to one or more of the networks via twisted pair wires, coaxial cable, fiber optics, radio waves or other communication media.

Computer software, hardware, and networks may be utilized in a variety of different system environments, including standalone, networked, remote-access (aka, remote desktop), virtualized, and/or cloud-based environments, among others.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 910, web server 906, and client computer 904, laptop 902. Data server 910 provides overall access, control and administration of databases and control software for performing one or more illustrative aspects described herein. Data serverdata server 910 may be connected to web server 906 through which users interact with and obtain data as requested. Alternatively, data server 910 may act as a web server itself and be directly connected to the internet. Data server 910 may be connected to web server 906 through the network 908 (e.g., the internet), via direct or indirect connection, or via some other network. Users may interact with the data server 910 using remote computer 904, laptop 902, e.g., using a web browser to connect to the data server 910 via one or more externally exposed web sites hosted by web server 906. Client computer 904, laptop 902 may be used in concert with data server 910 to access data stored therein, or may be used for other purposes. For example, from client computer 904, a user may access web server 906 using an internet browser, as is known in the art, or by executing a software application that communicates with web server 906 and/or data server 910 over a computer network (such as the internet).

Servers and applications may be combined on the same physical machines, and retain separate virtual or logical addresses, or may reside on separate physical machines. FIG. 9 illustrates just one example of a network architecture that may be used, and those of skill in the art will appreciate that the specific network architecture and data processing devices used may vary, and are secondary to the functionality that they provide, as further described herein. For example, services provided by web server 906 and data server 910 may be combined on a single server.

Each component data server 910, web server 906, computer 904, laptop 902 may be any type of known computer, server, or data processing device. Data server 910, e.g., may include a processor 912 controlling overall operation of the data server 910. Data server 910 may further include RAM 916, ROM 918, network interface 914, input/output interfaces 920 (e.g., keyboard, mouse, display, printer, etc.), and memory 922. Input/output interfaces 920 may include a variety of interface units and drives for reading, writing, displaying, and/or printing data or files. Memory 922 may further store operating system software 924 for controlling overall operation of the data server 910, control logic 926 for instructing data server 910 to perform aspects described herein, and other application software 928 providing secondary, support, and/or other functionality which may or may not be used in conjunction with aspects described herein. The control logic may also be referred to herein as the data server software control logic 926. Functionality of the data server software may refer to operations or decisions made automatically based on rules coded into the control logic, made manually by a user providing input into the system, and/or a combination of automatic processing based on user input (e.g., queries, data updates, etc.).

Memory 1122 may also store data used in performance of one or more aspects described herein, including a first database 932 and a second database 930. In some embodiments, the first database may include the second database (e.g., as a separate table, report, etc.). That is, the information can be stored in a single database, or separated into different logical, virtual, or physical databases, depending on system design. Web server 906, computer 904, laptop 902 may have similar or different architecture as described with respect to data server 910. Those of skill in the art will appreciate that the functionality of data server 910 (or web server 906, computer 904, laptop 902) as described herein may be spread across multiple data processing devices, for example, to distribute processing load across multiple computers, to segregate transactions based on geographic location, user access level, quality of service (QoS), etc.

One or more aspects may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a nonvolatile storage device. Any suitable computer readable storage media may be utilized, including hard disks, CD-ROMs, optical storage devices, magnetic storage devices, and/or any combination thereof. In addition, various transmission (non-storage) media representing data or events as described herein may be transferred between a source and a destination in the form of electromagnetic waves traveling through signal-conducting media such as metal wires, optical fibers, and/or wireless transmission media (e.g., air and/or space). various aspects described herein may be embodied as a method, a data processing system, or a computer program product. Therefore, various functionalities may be embodied in whole or in part in software, firmware and/or hardware or hardware equivalents such as integrated circuits, field programmable gate arrays (FPGA), and the like. Particular data structures may be used to more effectively implement one or more aspects described herein, and such data structures are contemplated within the scope of computer executable instructions and computer-usable data described herein.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus.

Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A method comprising:
   receiving a sample of interest at a mass spectrometry (MS) device for analysis;
   analyzing the sample of interest, the analyzing comprising generating a plurality of spectrums for the sample of interest;
   breaking the plurality of spectrums into bins;
   accessing a sample library comprising ionization information for known compounds;
   for each known compound in the sample library, retrieving a plurality of key peaks for the compound;
   receiving, as input, one or more of a user-defined number of bins for comparison to the key peaks, a user-defined value for the similarity threshold, or a user-defined bin weighting;
   comparing the key peaks for the respective compound to a set of bins from the sample of interest, the comparing comprising:
      representing the key peaks for the respective compound and the set of bins as vectors,
      computing a similarity value corresponding to a difference in angle between the vectors, and
      comparing the similarity value to the similarity threshold;
   identifying that the sample of interest is similar to the respective compound when the similarity value exceeds the similarity threshold; and
   outputting an indication that the sample of interest is similar to the respective compound in response to the identifying.

2. The method of claim 1, wherein the breaking the plurality of spectrums into bins comprises identifying peaks in the plurality of spectrums and generating bins corresponding to said peaks.

3. The method of claim 1, wherein the difference in angle between the vectors is represented as a cosine similarity value.

4. The method of claim 1, further comprising weighting the bins based on one or more of the spectrum intensity value or the mass associated with each bin.

5. The method of claim 1, further comprising weighting a bin from one of the plurality of spectrums over bins from others of the plurality of spectrums.

6. The method of claim 1, further comprising:
   for each of the bins, computing a ratio between an intensity of the bin and an intensity of a bin having the highest intensity value; and
   filtering out bins from analysis that have a ratio lower than a user-defined intensity ratio threshold.

7. A non-transitory computer-readable storage medium, the computer-readable storage medium including instructions that when executed by a computer, cause the computer to:
   receive a sample of interest at a mass spectrometry (MS) device for analysis;
   analyze the sample of interest, the analyzing comprising generating a plurality of spectrums for the sample of interest;
   break the plurality of spectrums into bins;
   access a sample library comprising ionization information for known compounds;
   for each known compound in the sample library, retrieve a plurality of key peaks for the compound;
   receiving, as input, one or more of a user-defined number of bins for comparison to the key peaks, a user-defined value for the similarity threshold, or a user-defined bin weighting;
   compare the key peaks for the respective compound to a set of bins from the sample of interest, the comparing comprising:
      represent the key peaks for the respective compound and the set of bins as vectors,
      compute a similarity value corresponding to a difference in angle between the vectors, and
      compare the similarity value to a similarity threshold;
   identify that the sample of interest is similar to the respective compound when the similarity value exceeds the similarity threshold; and
   output an indication that the sample of interest is similar to the respective compound in response to the identifying.

8. The computer-readable storage medium of claim 7, wherein the breaking the plurality of spectrums into bins comprises instructions which configure the computer to identify peaks in the plurality of spectrums and generate bins corresponding to said peaks.

9. The computer-readable storage medium of claim 7, wherein the difference in angle between the vectors is represented as a cosine similarity value.

10. The computer-readable storage medium of claim 7, wherein the instructions further configure the computer to weight the bins based on one or more of the spectrum intensity value or the mass associated with each bin.

11. The computer-readable storage medium of claim 7, wherein the instructions further configure the computer to weight a bin from one of the plurality of spectrums over bins from others of the plurality of spectrums.

12. The computer-readable storage medium of claim 7, wherein the instructions further configure the computer to:
for each of the bins, compute a ratio between an intensity of the bin and an intensity of a bin having the highest intensity value; and
filter out bins from analysis that have a ratio lower than a user-defined intensity ratio threshold.

13. A computing apparatus comprising:
a processor; and
a memory storing instructions that, when executed by the processor, configure the apparatus to:
receive a sample of interest at a mass spectrometry (MS) device for analysis;
analyze the sample of interest, the analyzing comprising generating a plurality of spectrums for the sample of interest;
break the plurality of spectrums into bins;
access a sample library comprising ionization information for known compounds;
for each known compound in the sample library, retrieve a plurality of key peaks for the compound;
receiving, as input, one or more of a user-defined number of bins for comparison to the key peaks, a user-defined value for the similarity threshold, or a user-defined bin weighting;
compare the key peaks for the respective compound to a set of bins from the sample of interest, the comparing comprising:
represent the key peaks for the respective compound and the set of bins as vectors,
compute a similarity value corresponding to a difference in angle between the vectors, and
compare the similarity value to a similarity threshold;
identify that the sample of interest is similar to the respective compound when the similarity value exceeds the similarity threshold; and
output an indication that the sample of interest is similar to the respective compound in response to the identifying.

14. The computing apparatus of claim 13, wherein the breaking the plurality of spectrums into bins comprises instructions which configure the apparatus to identify peaks in the plurality of spectrums and generate bins corresponding to said peaks.

15. The computing apparatus of claim 13, wherein the difference in angle between the vectors is represented as a cosine similarity value.

16. The computing apparatus of claim 13, wherein the instructions further configure the apparatus to perform one or more of:
weighting the bins based on one or more of the spectrum intensity value or the mass associated with each bin, or
weighting a bin from one of the plurality of spectrums over bins from others of the plurality of spectrums.

17. The computing apparatus of claim 13, wherein the instructions further configure the apparatus to:
for each of the bins, compute a ratio between an intensity of the bin and an intensity of a bin having the highest intensity value; and
filter out bins from analysis that have a ratio lower than a user-defined intensity ratio threshold.

* * * * *